(12) United States Patent
Trese et al.

(10) Patent No.: US 7,776,026 B2
(45) Date of Patent: Aug. 17, 2010

(54) METHOD FOR VITREOUS LIQUEFACTION

(75) Inventors: Michael T. Trese, Bloomfield Hills, MI (US); George A. Williams, Grosse Pointe Park, MI (US); Michael K. Hartzer, Rochester Hills, MI (US)

(73) Assignee: NuVue Technologies, Inc., Keene, NH (US)

( * ) Notice: Subject to any disclaimer, the term of this patent is extended or adjusted under 35 U.S.C. 154(b) by 917 days.

(21) Appl. No.: 10/068,314

(22) Filed: Feb. 6, 2002

(65) Prior Publication Data

US 2003/0147877 A1 Aug. 7, 2003

(51) Int. Cl.
*A61F 9/00* (2006.01)
*A61M 31/00* (2006.01)

(52) U.S. Cl. ............... 604/521; 604/500; 604/506; 606/107

(58) Field of Classification Search ............... 666/167, 666/107; 604/521, 500, 506, 518, 264, 508; 128/898; 606/167, 107
See application file for complete search history.

(56) References Cited

U.S. PATENT DOCUMENTS

| 4,299,227 A | 11/1981 | Lincoff | 128/898 X |
|---|---|---|---|
| 4,328,803 A | 5/1982 | Pape | 128/898 X |
| 4,764,466 A | 8/1988 | Suyama et al. | 435/174 |
| 4,853,224 A | 8/1989 | Wong | 424/427 |
| 4,997,652 A | 3/1991 | Wong | 424/428 |
| 5,002,571 A | 3/1991 | O'Donnell, Jr. et al. | 623/6 |
| 5,047,008 A | 9/1991 | de Juan, Jr. et al. | 604/22 |
| 5,066,276 A | 11/1991 | Wang | 604/51 |
| 5,120,307 A | 6/1992 | Wang | 604/51 |
| 5,178,635 A | 1/1993 | Gwon et al. | 623/4 |
| 5,182,259 A | 1/1993 | Kita | 604/290 X |
| 5,244,799 A | 9/1993 | Anderson | 435/240.23 |
| 5,304,118 A | 4/1994 | Trese et al. | 604/51 |

OTHER PUBLICATIONS

Shi et al., Posterior vitreous detachment with plasmin in the isloated human eye, Jan. 2002, Graefes Arch Clin Exp Ophthalmol, 240(1):56-62.*
Trese et al., A New Approach to Stage 3 Macular Holes, Aug. 2000, Ophthalmology, 107(8):1607-11.*
Gandorfer et al., Ultrastrcuture of the vitreorentinal interface following plasmin assisted vitrectomy, Jan. 2001, Br J Ophthalmol. 85(1):6-10.*
Trese et al., Sep. 1, 2004, Ophthalmology, vol. 105, Issue 9, pp. 1617-1620.*
U.S. Appl. No. 09/820,159, filed Mar. 28, 2001, Trese et al.

* cited by examiner

*Primary Examiner*—Matthew F DeSanto
(74) *Attorney, Agent, or Firm*—Gifford, Krass, Sprinkle, Anderson & Citkowski, P.C.

(57) ABSTRACT

A process is disclosed for liquefying the vitreous humor of an eye. The process includes the steps of delivering plasmin into the vitreous of the eye and incubating the vitreous and plasmin together for a period of time. Plasmin may be introduced through injection or a sustained release device. Plasmin may be used to treat a pathological condition of the eye such as diabetic retinopathy, macular hole, macular pucker, intraocular infection, foreign intraocular material and retinal detachment.

24 Claims, 1 Drawing Sheet

METHOD FOR VITREOUS LIQUEFACTION

FIELD OF THE INVENTION

The present invention relates generally to a process for using a protease in an ophthalmic procedure. More particularly, the present invention relates to a process for using plasmin to liquefy the vitreous humor of an eye during a vitrectomy.

BACKGROUND OF THE INVENTION

The vitreous humor, or vitreous, is a semi-solid material having a gel-like consistency that fills the vitreous cavity, which is approximately the space in the eye between the lens and the retina. Surgical removal of the vitreous, vitrectomy, is sometimes necessary in order to treat certain medical diseases and/or dysfunctions of the eye. Typically, a vitrectomy involves the removal of the vitreous humor using mechanical instrumentation to detach and aspirate the vitreous from the eye while simultaneously replacing the removed vitreous with a sterile material such as a saline solution to prevent collapse of the eye.

One difficulty in performing a vitrectomy is that the vitreous consistency is often so viscous as to make the removal difficult, even with the use of mechanical suction or cutting. This is particularly true when using modem microsurgical vitreous instrumentation, such as that smaller than 20 gauge. It may be desirable to use small gauge instrumentation whenever possible during ophthalmic surgery in order to avoid mechanical damage to ocular tissues. However, small gauge instrumentation is easily clogged by the vitreous gel, resulting in traction on the retina which leads to the possibility of tearing or other retinal damage. This, of course, is highly undesirable since such damage may compromise the patient's visual outcome following vitrectomy.

Thus, there exists a need for a process to liquefy and reduce the viscosity of the vitreous body so that a vitrectomy can be performed in a safer and more reproducible manner.

SUMMARY OF THE INVENTION

A process is detailed that includes steps of administration of plasmin into the vitreous of an eye and the incubation of the plasmin in the vitreous such that the vitreous is liquefied. A plasmin composition is administered into the vitreous by injection, infusion or via a sustained release device. Preferably, the plasmin is autologous human plasmin that is optionally administered in conjunction with an enzyme, a glycoprotein, a polysaccharide, an antibiotic, a pharmaceutically acceptable diluent, a pharmaceutically acceptable adjuvant and a pharmaceutically acceptable carrier. An optional step in the process described is the administration of a plasmin inhibitor. A preferred dose of a plasmin composition includes 0.01-5 units of plasmin which is administered and incubated for a time ranging from 10 minutes to 2 hours.

DETAILED DESCRIPTION OF THE PREFERRED EMBODIMENTS

Figure 1:
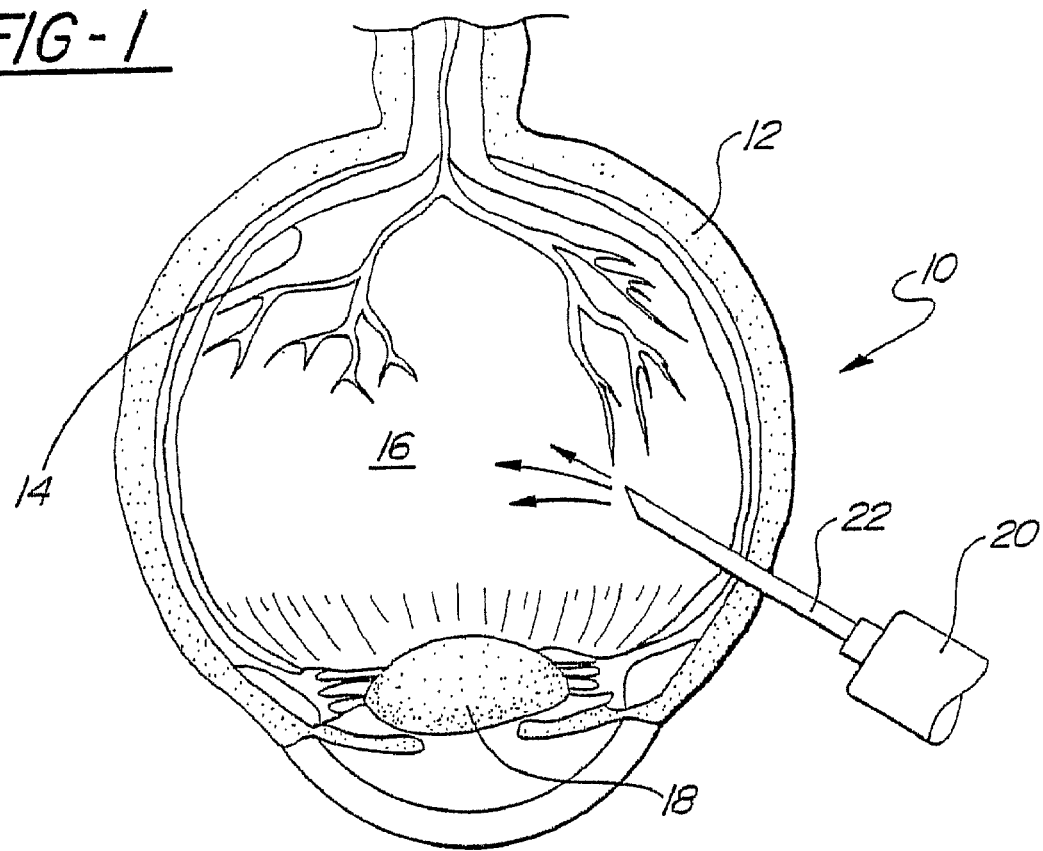
FIG. 1 is a cross sectional view of an eye undergoing liquefaction according to a process of the present invention.

In a method of the present invention plasmin is used to assist in vitrectomy by liquefying the vitreous. Collagenase,[7] dispase,[8] chondroitinase,[9] hyaluronidase,[10] and plasmin[3,4] have all demonstrated enzymatic activity towards components of the vitreous or vitreoretinal juncture. Plasmin is a nonspecific protease best known for its fibrinolytic properties but which is also associated with cleavage of laminin, fibronectin, and other components of the vitreoretinal juncture[1,2]. It has been demonstrated that intravitreal injection of plasmin facilitates the formation of a posterior vitreous separation in rabbits.[3,4] Additionally, plasmin facilitates the closure of traumatic pediatric macular holes[5,11] and aids in surgical management of diabetic retinopathy[12]. Plasmin administration and resulting vitreous liquefaction is used in management of various pathological conditions of the eye that are typically treated by at least partial removal of the vitreous humor including diabetic retinopathy, macular hole, macular pucker, intraocular infection, removal of foreign intraocular material and retinal detachment.

With reference to the drawing, an eye (10) such as a human eye is shown in which the sclera (12) forms a generally spherical outer body for the eye (10). A retina (14) extends along the inside rear surface of the eye wall (12) while vitreous humor (16) fills the volume of the eye wall (12) posteriorly to the natural eye lens (18).

In a vitrectomy, the vitreous (16) is removed and replaced by a sterile solution. In accordance with the present invention, plasmin (20) is introduced into the vitreous (16) by any conventional means such as through a hypodermic needle (22) and allowed to incubate for a period of time, causing liquefaction. Following liquefaction of the vitreous (16), it is removed from the eye by conventional means. Furthermore, due to the liquefaction of the vitreous (16), it can be easily removed with reduced risk of tearing of the retina (14). In addition, removal of the vitreous from the eye can be achieved with microsurgical instrumentation (24), such as 25 gauge or smaller.

Plasmin Dose

The dosage of plasmin used is a factor in determining the cell and tissue effects of the enzyme. For example, relatively high concentrations of plasmin injected intraocularly result in posterior vitreous detachment[3,4] while lower concentrations have differential effects on matrix metalloprotease (MMP) enzyme activities. On the other hand, adding plasmin treatment to vitreous at 37° C. produces an increase in MMP-1 activity. Plasmin at the therapeutic concentrations detailed herein offers the potential therapeutic advantage of at least partially liquefying the vitreous humor and thus decreasing its viscosity. As used herein, a unit is defined in terms of activity per milliliter based upon the difference between initial and final optical absorbance multiplied by a constant for the cleavage of a synthetic substrate (D-val-leu-lys-pnitroanilide dihydrochloride) measured at a wavelength of 405 nanometers. Absorption studies for example are performed by adding 950 µl of lysine buffer and 250 µl of substrate to a cuvette and zeroing the initial absorbance. 50 µl of plasmin is then added and the absorbance one minute later is measured as the final absorbance. The exact dosage of plasmin will vary from subject to subject and depends on multiple factors including the volume of the subject's vitreous body, the initial viscosity of the vitreous, the desired treatment time and the condition to be treated. For example, in a pediatric patient where the volume of the eye is significantly smaller, a dose of 0.4 units may result in facilitating posterior vitreous detachment.[5] Thus, in order to liquefy the vitreous in a patient with a smaller eye volume, the usual dose is decreased. In general, a plasmin dose of 0.01-5 units is administered to a subject to liquefy the vitreous. More preferably, a dose of between 0.1-1.0 unit of plasmin is administered.

Treatment Time

A plasmin composition can be introduced into the eye prior to the vitrectomy depending on the initial viscosity of the vitreous, the age and general health of the subject among other factors.

A suitable incubation time for a plasmin composition in the eye before vitrectomy is determined by one of skill in the art. For example, following administration of plasmin, a suitable incubation time is determined by periodic testing of vitreous viscosity following plasmin administration by mechanical manipulation of the vitreous in situ. Further, the extent to which vitreous liquefaction is taking place after introduction of plasmin is determined by observing the differential mixing of the fluids of differing viscosity known as schlieren lines which will be apparent to an ophthalmic surgeon as changes in the vitreous occur. Generally, a plasmin composition is introduced into the eye ten minutes to two hours before the bulk of the vitrectomy is performed. Preferably, a plasmin composition is introduced into the eye about ten minutes to about an hour before the vitreous is removed.

Plasmin Composition

A plasmin composition of the present invention includes mammalian plasmin and preferably human plasmin. Most preferably, the included plasmin is autologous human plasmin. Autologous human plasmin is generated by any of several methods, for example, according to a method of U.S. Pat. No. 6,207,066, using a kit as detailed in U.S. Pat. No. 6,183,692 or according to a method described in Example 1.

A plasmin composition of the present invention will further contain a pharmaceutically acceptable carrier and, in addition, may include other medicinal agents, pharmaceutical agents, carriers, or diluents. An injectable plasmin composition can be prepared in conventional forms, either liquid solutions or suspensions, solid forms suitable for solution or prior to injection, or as suspension in liquid prior to injection or as emulsions. Liquid pharmaceutically administrable compositions can, for example, be prepared by dissolving or dispersing plasmin with optimal pharmaceutical adjuvants in an excipient, such as water or saline, to thereby form a solution. If desired, a plasmin composition to be administered may also contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see *Remington's Pharmaceutical Sciences*. It is appreciated that plasmin delivery to the vitreous is optionally accompanied by another enzyme, glycoprotein, polysaccharide, antibiotic, pharmaceutically acceptable diluent, adjuvant and carrier.

Administration of a Plasmin Composition

Injection or infusion are preferred methods of delivery for a single dose of a plasmin composition. Injection and infusion methods of administration into the eye are well known in the art. In some cases, it may be advantageous to remove a portion of aqueous humor to eliminate excessive intraocular pressure, before or contemporaneous with injection or infusion of a plasmin composition. Prolonged or repeated dosages according to the present invention are delivered by injection, infusion or, alternatively, delivered by a sustained release device such as that shown in U.S. Pat. No. 4,135,514.

Optionally, a plasmin inhibitor is administered after the desired level of vitreous liquefaction is attained. Any of various inhibitors of plasmin activity are used such as, an antiplasmin antibody or an endogenous inhibitor alpha2 antiplasmin. Administration of an inhibitor is by injection, infusion or sustained release device as above.

In order to more fully demonstrate the advantages arising from the present invention, the following examples are set forth. It is to be understood that the following is by way of example only and not intended as a limitation on the scope of the invention.

EXAMPLES

Example 1

Preparation of Human Plasmin

Autologous human plasmin is isolated by drawing patient blood before surgery and isolating plasminogen from the human plasma by affinity chromatography on a lysine-Sepharose column (Sigma Chemical). After elution of the plasminogen from the column by 15 mM aminocaproic acid (Amicar, American Reagent Laboratories), the plasminogen is dialyzed for three hours, or overnight, against 100 mM NaCl, 100 mM d-mannitol, 20 mM $Na_2HPO_4$, pH 7.5 to remove the aminocaproic acid. The plasminogen is concentrated to a volume of 0.6 ml, 50,000 IU of streptokinase (Streptase, Astra) added and the mixture is incubated at 37° C. for ten minutes. Plasmin activity is determined spectrophotometrically by measuring the cleavage of a synthetic substrate (D-val-leu-lys-p-nitroanilide hydrochloride, Sigma Chemical) which gives an absorbance at 405 nm. Plasmin is stored at 4° C. or −70° C. until used.

Example 2

In Vivo Use

A patient is prepared for vitrectomy as is standard. Ten minutes prior to surgical incision, 0.8 IU autologous plasmin in a volume of 0.1 cc is injected into the mid vitreous using a 30 ga needle and tuberculin syringe. Optionally, prior to injection, a paracentesis is performed to prevent an increase in intraocular pressure. The eye is entered using an infusion/fiber optic light source and the state of vitreous liquefaction determined by assessing schlieren line presence. Suction is used to remove vitreous through a narrow gauge instrument.

REFERENCES

1. Liotta L A, Goldfarb R H, Brundage R, Siegal G P, Terranova V, Garbisa. Effect of plasminogen activator (urokinase), plasmin, and thrombin on glycoprotein and collagenous components of basement membrane. Cancer Res 1981; 41:4629-4636.
2. Papp, B Kovacs, T, Lerent, I et al. Conditions of formation of the heparin-fibronectin-collagen complex and the effect of plasmin. Biochim Biophys Acta 1987; 925:241-247.
3. Verstraeten T C, Chapman C, Hartzer M, et al. Pharmacologic induction of posterior vitreous detachment in the rabbit. Arch Ophthalmol 1993; 111:849-54.
4. Hikichi T, Yanagiya N, Kado M. Posterior vitreous detachment induced by injection of plasmin and sulfur hexafluoride in the rabbit vitreous. Retina 1999; 19:55-58.
5. Margherio A R, Margherio R R, Hartzer M, et al. Plasmin enzyme-assisted vitrectomy in traumatic pediatric macular holes. Ophthalmology 1998; 105:1617-1620.

6. Williams G A. Pharmacologic manipulation of the vitreous during pars plana vitrectomy. In: Alfaro III D V & Liggett P E, eds. Vitreoretinal surgery of the injured eye. Philadelphia: Lippincott-Raven Publishers, 1999.
7. Moorehead L C, Redburn D A, Kirkpatrick D S, et al. Bacterial collagenase: proposed adjunct to vitrectomy with membranectomy. Arch Ophthalmol 1980; 98: 1829-39.
8. Tezel T H, Del Priore L V, Kaplan H J. Posterior vitreous detachment with dispase. Retina 1998:18:7-15.
9. Hageman G S, Russell S R. Chondroitinase-mediated disinsertion of the primate vitreous body. [ARVO Abstract] Invest Ophthalmol Vis Sci 1994; 35: S1260, Abstract nr.
10. Harooni M, McMillan T, Refojo M. Efficacy and safety of enzymatic posterior vitreous detachment by intravitreal injection of hyaluronidase. Retina 1998; 18:16-22.
11. Chow D R, Williams G A, Trese M T, Margherio R R, Ruby A J, Successful closure of traumatic macular holes. Retina 1999; 19:405-9.
12. Williams J G, Trese, M T, Williams, G A, Hartzer, M K, Autologous plasmin enzyme in the surgical management of diabetic retinopathy. Ophthalmology 2001; 108:1902-5.

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for human vitreous liquefaction comprising the steps of:
    delivering a dose of plasmin in a range of less than 0.4 units to 0.01 units and in a volume of about 0.1 cubic centimeters into a vitreous body of a subject human eye; and
    incubating the plasmin in the vitreous body for a predetermined amount of time to create a liquefied vitreous.

2. The process of claim 1 wherein the subject eye has a pathological condition.

3. The process of claim 2 wherein the pathological condition is selected from the group consisting of: diabetic retinopathy, macular hole, macular pucker, intraocular infection, foreign intraocular material and retinal detachment.

4. The process of claim 1 further comprising the step of suctioning the liquefied vitreous from the subject human eye.

5. The process of claim 4 wherein suctioning is performed through a 25 or finer gauge instrument.

6. The process of claim 1 wherein the delivering is by injection.

7. The process of claim 1 wherein the delivering is by infusion.

8. The process of claim 1 wherein the delivering is by sustained release intraocular device.

9. The process of claim 1 wherein the plasmin comprises human plasmin.

10. The process of claim 1 wherein the plasmin comprises autologous human plasmin.

11. The process of claim 1 wherein the plasmin comprises an accompaniment selected from the group consisting of: an enzyme, a glycoprotein, a polysaccharide, an antibiotic, a pharmaceutically acceptable diluent, a pharmaceutically acceptable adjuvant and a pharmaceutically acceptable carrier.

12. The process of claim 1 further comprising the step of delivering a plasmin inhibitor.

13. The process of claim 1 wherein the predetermined amount of time is ten minutes and two hours.

14. A process for human vitreous liquefaction comprising the steps of:
    delivering a dose of plasmin in a range of less than 0.4 units to 0.01 units and in a volume of about 0.1 cubic centimeters comprising autologous plasmin into a vitreous body of a subject human eye; and
    incubating the plasmin in the vitreous body for a predetermined amount of time to induce vitreous liquefaction.

15. The process of claim 14 wherein the subject eye has a pathological condition.

16. The process of claim 15 wherein the pathological condition is selected from the group consisting of: diabetic retinopathy, macular hole, macular pucker, intraocular infection, foreign intraocular material and retinal detachment.

17. The process of claim 14 further comprising the step of suctioning the liquefied vitreous from the subject human eye.

18. The process of claim 17 wherein suctioning is performed through a 25 or finer gauge instrument.

19. The process of claim 14 wherein the delivering is by injection.

20. The process of claim 14 wherein the delivering is by infusion.

21. The process of claim 14 wherein the delivering is by sustained release intraocular device.

22. The process of claim 14 wherein the plasmin comprises an accompaniment selected from the group consisting of: an enzyme, a glycoprotein, a polysaccharide, an antibiotic, a pharmaceutically acceptable diluent, a pharmaceutically acceptable adjuvant and a pharmaceutically acceptable carrier.

23. The process of claim 14 further comprising the step of delivering a plasmin inhibitor.

24. The process of claim 14 wherein the predetermined amount of time is ten minutes and two hours.

* * * * *